US012601733B2

(12) United States Patent
Wang et al.

(10) Patent No.: US 12,601,733 B2
(45) Date of Patent: Apr. 14, 2026

(54) DEVICES FOR PERITONEAL DIALYSATE ANALYSIS

(71) Applicant: AWAK TECHNOLOGIES PTE LTD, Singapore (SG)

(72) Inventors: Yue Wang, Singapore (SG); Peter Haywood, Singapore (SG); Suresha Belur Venkataraya, Singapore (SG); Mandar Manohar Gori, Singapore (SG)

(73) Assignee: AWAK TECHNOLOGIES PTE LTD, Singapore (SG)

( * ) Notice: Subject to any disclaimer, the term of this patent is extended or adjusted under 35 U.S.C. 154(b) by 526 days.

(21) Appl. No.: 18/003,205

(22) PCT Filed: Jun. 28, 2021

(86) PCT No.: PCT/SG2021/050373
§ 371 (c)(1),
(2) Date: Dec. 23, 2022

(87) PCT Pub. No.: WO2022/005397
PCT Pub. Date: Jan. 6, 2022

(65) Prior Publication Data
US 2023/0248890 A1      Aug. 10, 2023

(30) Foreign Application Priority Data
Jul. 1, 2020    (SG) ............................ 10202006355P

(51) Int. Cl.
*G01N 33/50*        (2006.01)
*A61B 5/00*        (2006.01)
(Continued)

(52) U.S. Cl.
CPC ......... *G01N 33/50* (2013.01); *A61B 5/14532* (2013.01); *A61B 5/14546* (2013.01);
(Continued)

(58) Field of Classification Search
CPC . A61B 5/14532; A61B 5/14546; A61B 5/201; A61B 5/4848; A61B 5/6823;
(Continued)

(56) References Cited

U.S. PATENT DOCUMENTS

| | | | |
|---|---|---|---|
| 10,646,850 | B2 | 5/2020 | Kanda et al. |
| 2003/0216677 | A1 | 11/2003 | Pan et al. |
| 2018/0193546 | A1 | 7/2018 | Gerber et al. |

FOREIGN PATENT DOCUMENTS

| | | |
|---|---|---|
| CN | 108290156 A | 7/2018 |
| JP | 2020518302 A | 6/2020 |

(Continued)

OTHER PUBLICATIONS

First Office Action cited in corresponding Chinese Application No. 20218006148.5, dated Mar. 14, 2025.
(Continued)

*Primary Examiner* — John Kim
(74) *Attorney, Agent, or Firm* — LEASON ELLIS LLP

(57)        ABSTRACT

The present disclosure generally relates to a device for analysing spent peritoneal dialysate from a peritoneal dialysis apparatus. The device comprises: a set of housings attachable to the peritoneal dialysis apparatus; a set of test components disposed in the housings, each test component and comprising one or more reagents for detecting one or more substances; and a set of fluidic conduits connected to the housings for communicating the dialysate from the peritoneal dialysis apparatus to the housings, wherein the test components are arranged for the reagents to react with the dialysate communicated to the housings and thereby detect the substances in the dialysate.

13 Claims, 14 Drawing Sheets

(51) Int. Cl.

| | |
|---|---|
| *A61B 5/145* | (2006.01) |
| *A61B 5/20* | (2006.01) |
| *A61M 1/16* | (2006.01) |
| *A61M 1/28* | (2006.01) |
| *G16H 10/40* | (2018.01) |

(52) U.S. Cl.
CPC ............ *A61B 5/201* (2013.01); *A61B 5/4848* (2013.01); *A61B 5/6823* (2013.01); *A61B 5/6866* (2013.01); *A61M 1/1609* (2014.02); *A61M 1/28* (2013.01); *A61M 1/284* (2014.02); *G16H 10/40* (2018.01); *A61M 2205/33* (2013.01)

(58) Field of Classification Search
CPC ..... A61B 5/6866; A61M 1/1609; A61M 1/28; A61M 1/284; A61M 2205/18; A61M 2205/33; A61M 2205/3553; A61M 2205/3561; A61M 2205/3576; A61M 2205/584; G01N 33/50; G16H 10/40
See application file for complete search history.

(56) References Cited

FOREIGN PATENT DOCUMENTS

| | | | |
|---|---|---|---|
| WO | 2018047929 | A1 | 3/2018 |
| WO | 2018142406 | A1 | 8/2018 |
| WO | 2020084042 | A1 | 4/2020 |

OTHER PUBLICATIONS

Office Action cited in corresponding Japanese Application No. 2022-581534, dated Feb. 28, 2025.

International Preliminary Report on Patentability cited in corresponding International Application No. PCT/SG2021/050373, dated Oct. 4, 2022.

International Search Report and Written Opinion for corresponding International Application No. PCT/SG2021/050373, dated Sep. 24, 2021.

Office Action cited in corresponding Korean Application No. 10-2023-7002847, dated Nov. 6, 2025 (English Translation), 9 pages.

Second Office Action cited in corresponding Chinese Application No. 202180061481.5, dated Sep. 19, 2025, with English Translation, 20 pages.

Second Office Action cited in corresponding Japanese Application No. 2022-581534, dated Sep. 25, 2025, with English Translation, 14 pages.

200

200

400

400

800

810

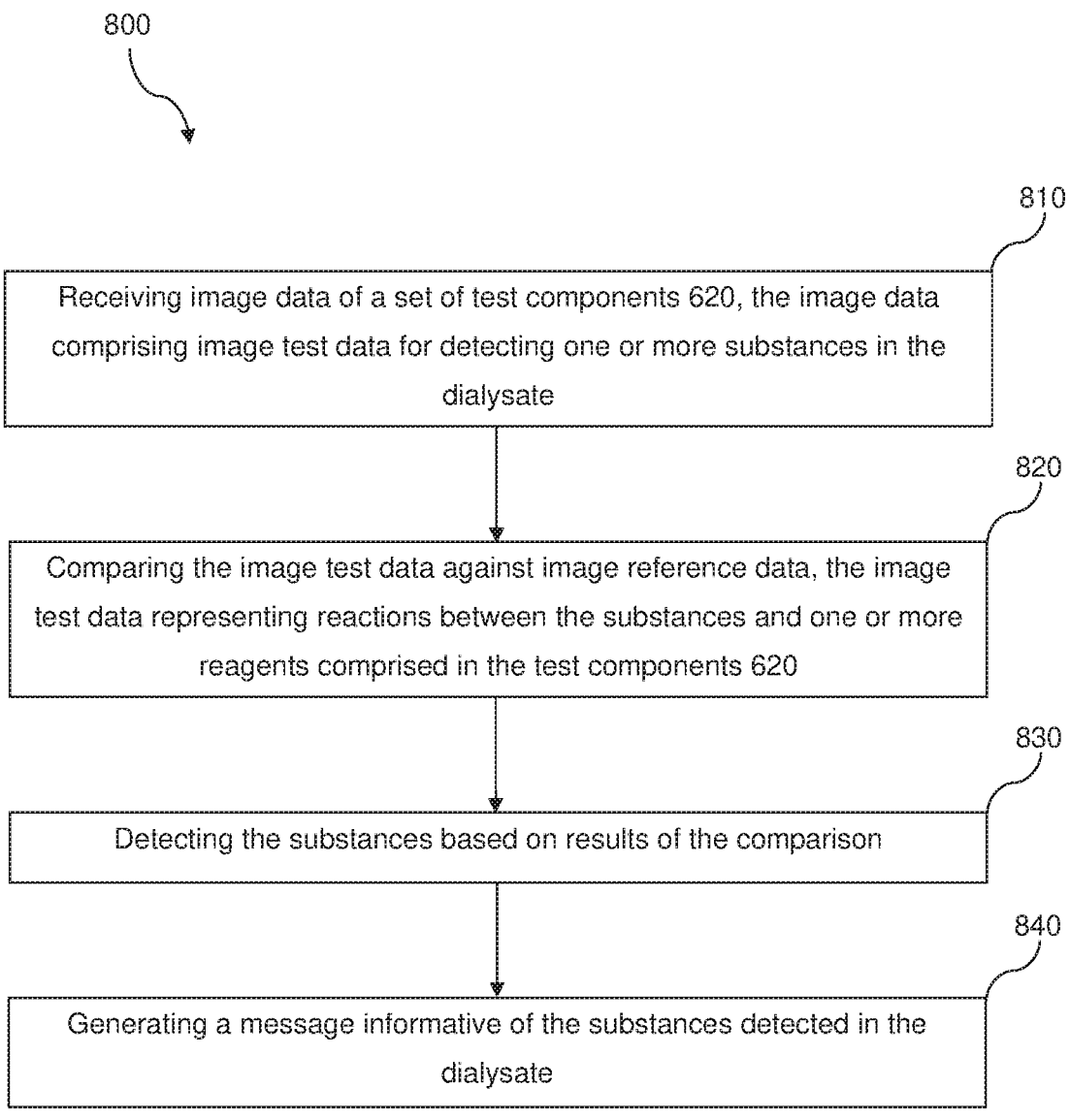

Receiving image data of a set of test components 620, the image data comprising image test data for detecting one or more substances in the dialysate

820

Comparing the image test data against image reference data, the image test data representing reactions between the substances and one or more reagents comprised in the test components 620

830

Detecting the substances based on results of the comparison

840

Generating a message informative of the substances detected in the dialysate

Figure 8

DEVICES FOR PERITONEAL DIALYSATE ANALYSIS

CROSS-REFERENCE TO RELATED PATENT APPLICATIONS

This application is a U.S. National Stage Application under 35 U.S.C. § 371 of International Patent Application No. PCT/SG2021/050373 filed Jun. 28, 2021, which claims the benefit of priority of Patent Application numbers SG 10202006355P filed Jul. 1, 2020, both of which are incorporated by reference in their entireties. The International Application was published on Jan. 6, 2022, as International Publication No. WO/2022/005397.

TECHNICAL FIELD

The present disclosure generally relates to devices for peritoneal dialysate analysis. More particularly, the present disclosure describes various embodiments of a device useable with a peritoneal dialysis apparatus for analysing spent peritoneal dialysate from the peritoneal dialysis apparatus.

BACKGROUND

Millions of people worldwide suffer from kidney-related problems, e.g. chronic kidney disease (CKD), and require treatment with dialysis or a kidney transplant to stay alive. There are two modalities of dialysis—haemodialysis and peritoneal dialysis. In haemodialysis, blood is pumped out of the patient's body to a dialysis machine which filters the blood and returns the filtered blood to the body. In peritoneal dialysis, the peritoneum in the patient's abdomen acts as a natural filtration membrane. Haemodialysis is more commonly used than peritoneal dialysis because of several factors including reimbursement landscape, infrastructure investment and utilization. Comparatively, peritoneal dialysis although less commonly used, is increasingly being adopted around the world. Some countries have implemented policies that recommend or mandate using peritoneal dialysis first, especially as an introductory therapy for CKD patients.

FIG. 1 illustrates an exemplary peritoneal dialysis apparatus 100 used by a patient 102 at home. The patient 102 would have a catheter 104 placed into the abdomen prior to peritoneal dialysis. To begin peritoneal dialysis, the patient 102 connects a transfer set tubing 106 to the catheter 104 and to a three-way connector or Y-connector 108. The transfer set tubing 106 has a valve to open and close the catheter 104 which should normally be closed to prevent infection. A bag of fresh dialysis solution 110 is connected to the Y-connector 108 via a supply tubing 113. The Y-connector 108 is further connected to a drain bag 112 via a drain tubing 114.

During peritoneal dialysis, the fresh dialysis solution 110 flows into the abdomen where the peritoneum allows waste compounds and excess fluid to pass from the blood into the fresh dialysis solution 110. The fresh dialysis solution 110 contains a sugar such as glucose/dextrose that acts as the main osmotic agent to achieve fluid removal or filtration across the peritoneum into the abdominal cavity. The used dialysis solution is discharged from the body as spent peritoneal dialysate which contains the waste compounds and excess fluid. The spent peritoneal dialysate is collected in the drain bag 112 and thrown away.

An important advantage of receiving peritoneal dialysis treatment is that patients can receive the therapy on the go without an extreme compromise to their quality of life.

Peritoneal dialysis is also generally perceived as a gentler therapy than haemodialysis. The long intervals between haemodialysis therapies means that patients undergoing peritoneal dialysis are less haemodynamically challenged than patients undergoing haemodialysis. This makes peritoneal dialysis suitable and attractive as an introductory therapy or as a treatment option for vulnerable patients such as the elderly.

However, one problem in peritoneal dialysis is the limited duration for which patients can undergo peritoneal dialysis. The mean duration that patients are able to remain on peritoneal dialysis is 3 to 5 years. This is due to gradual degradation of the peritoneum after years of usage, and the peritoneum eventually becomes too permeable to glucose/dextrose. As such, the natural filtering ability of the peritoneum is diminished and excess fluid, electrolytes and toxins can no longer be cleared effectively. At this point, patients are forced to transition to haemodialysis to survive. This may not be a desirable scenario especially for the elderly as haemodialysis is an inherently more burdensome and physiologically challenging regimen than peritoneal dialysis.

One of the primary causes of degradation of the peritoneum are the persistent and frequent episodes of infection, or peritonitis, that patients might suffer during their course of dialysis. The immune systems of patients are often compromised due to dialysis-related poor nutritional status and reduced organ function, and as such they are vulnerable to infection. Extreme care and compliance are required with hygiene practices in place for daily peritoneal dialysis treatments, which involves multiple tubing connections and disconnections. If patients do not follow good hygiene practice, they may suffer an increased incidence of peritonitis infections. Peritonitis is difficult to diagnose clinically in patients undergoing peritoneal dialysis as clinical signs and symptoms of peritonitis, such as abdominal pain, distension, and tenderness of the abdomen, may be caused by non-infectious factors such as regular filling of the abdominal cavity with peritoneal dialysate. A significant number of patients with peritonitis may not show symptoms during the early stages of the infection, leading to a delay in diagnosis and treatment.

The current clinical practice depends on patients checking the visual appearance of the dialysate for an initial indication of peritonitis. Presence of bacteria, mycobacteria, fungi, and parasites in the peritoneum can trigger generation of white blood cells or leukocytes which accumulate in the dialysate, giving it a cloudy colour or turbid appearance. The reliance on a visual turbidity check introduces some shortcomings. Firstly, the visual check is subjective and reliant on the eyesight and opinion of the patient. Secondly, turbidity is not a specific indication of peritonitis infection and can be attributed to other factors. For example, cloudiness or turbid appearance of the dialysate can be caused by non-pathogenic processes such as general immune reaction, spontaneous fibrin generation, and pneumoperitoneum. A high-fat diet may also result in accumulation of lipoproteins and triglycerides, inducing a milky-white coloured dialysate and confounding the visual diagnosis of peritonitis.

Even if the patient observes turbidity in the dialysate in this semi-qualitative visual test, certain parameters of the dialysate must still be measured for accurate diagnosis of peritonitis. These parameters include the total leukocyte count (e.g. more than 100 cells/µL), absolute neutrophil count (e.g. more than 50%), and microbial culture of the dialysate. If the patient is indeed suffering from peritonitis or more specifically spontaneous bacterial peritonitis, the appearance of the dialysate tends to be cloudy and turbid due to the excess leukocytes in the dialysate, but this cannot be the sole determinant of peritonitis as other factors can also cause similar changes in dialysate appearance. The patient suffering from peritonitis will need rapid treatment with antibiotics but these investigations require time and are usually not available at home, which conflicts with the home-based setting of peritoneal dialysis therapy. The patient will instead have to deliver a sample of the dialysate to a clinic or hospital where these parameters will be measured. This can potentially result in loss of opportunity to promptly detect and treat peritonitis.

Peritonitis can be quickly diagnosed in hospitals and clinics by clinicians using a leukocyte esterase reagent strip. Leukocyte esterase activity in peritoneal dialysis increases when leukocyte counts increase in response to peritoneal infections. The strips are not ideal for patients to use at home as several preparation steps are required. Particularly, the patient has to collect a smaller sample of the drained dialysate which is not user-friendly and might cause additional exposure to infection. Additionally, patients and carers will require training and sufficient dexterity for proper sample handling in order to prevent contamination of the dialysate sample which may result in incorrect diagnosis.

In view of the importance of peritoneal dialysis and especially for patients suffering from CKD, current methods of diagnosing peritonitis are inadequate and could cause patients to delay treatment, potentially placing their health and lives in danger. Therefore, in order to address or alleviate at least one of the aforementioned problems and/or disadvantages, there is a need to provide improved devices for analysing spent peritoneal dialysate, wherein results of the analysis can be used to quickly diagnose peritonitis.

SUMMARY

Various aspects of the present disclosure are described below.

Clause 1. A device for analysing spent peritoneal dialysate from a peritoneal dialysis apparatus, the device comprising:
a set of housings attachable to the peritoneal dialysis apparatus;
a set of test components disposed in the housings, each test component and comprising one or more reagents for detecting one or more substances; and
a set of fluidic conduits connected to the housings for communicating the dialysate from the peritoneal dialysis apparatus to the housings,
wherein the test components are arranged for the reagents to react with the dialysate communicated to the housings and thereby detect the substances in the dialysate.
Clause 2. The device according to Clause 1, comprising:
a plurality of the housings attachable to the peritoneal dialysis apparatus;
a plurality of the test components disposed in the housings: and
a plurality of fluidic conduits each connected to a respective housing.
Clause 3. The device according to Clause 1 or 2, wherein the housings are attachable to the peritoneal dialysis apparatus by connecting the fluidic conduits to one of the following:
(a) a drain bag for collecting the dialysate discharged from the peritoneal dialysis apparatus;
(b) a transfer set tubing for connecting to a catheter of the peritoneal dialysis apparatus; and
(c) a drain tubing for discharging the dialysate.

Clause 4. The device according to Clause 1 or 2, wherein the housings are attachable inside a drain bag of the peritoneal dialysis apparatus for collecting the dialysate discharged therefrom, the fluidic conduits arranged for communicating the dialysate from the drain bag to the housings.
Clause 5. The device according to Clause 4, further comprising the drain bag wherein the housings are attached inside the drain bag.
Clause 6. The device according to any one of Clauses 1 to 5, wherein the fluidic conduits are configured for regulating communication of the dialysate to the housings.
Clause 7. The device according to any one of Clauses 1 to 6, wherein the fluidic conduits comprise a set of frangible seals that fluidically isolates the housings, and wherein the frangible seals are breakable to enable communication of the dialysate to the housings.
Clause 8. The device according to any one of Clauses 1 to 7, wherein the fluidic conduits comprise a set of semipermeable membranes for regulating communication of the dialysate to the housings.
Clause 9. The device according to any one of Clauses 1 to 8, further comprising a valve mechanism for selectively controlling communication of the dialysate through the fluidic conduits.
Clause 10. The device according to any one of Clauses 1 to 9, further comprising a set of mesh components disposed in the housings for regulated wetting of the test components by the dialysate.
Clause 11. The device according to Clause 1 or 2, further comprising a drain bag attachable to the peritoneal dialysis apparatus for collecting the dialysate discharged therefrom, wherein the housings are attached to an outer surface of the drain bag.
Clause 12. The device according to Clause 11, wherein each fluidic conduit comprises a perforated area for communicating the dialysate from the drain bag to the housings through the outer surface of the drain bag.
Clause 13. The device according to Clause 1, comprising a single housing comprising one of the following:
(a) a drain bag for collecting the dialysate discharged from the peritoneal dialysis apparatus;
(b) a transfer set tubing for connecting to a catheter of the peritoneal dialysis apparatus; and
(c) a drain tubing for discharging the dialysate.
Clause 14. The device according to Clause 13, wherein the test components are attached to an inner surface of the housing.
Clause 15. The device according to Clause 14, further comprising a set of inner layers attached to the inner surface of the housing and covering the test components, each inner layer optionally comprising semipermeable membrane for regulating communication of the dialysate to a respective test component.
Clause 16. The device according to Clause 13, wherein the reagents are deposited on the inner surface of the housing.
Clause 17. The device according to any one of Clauses 1 to 16, wherein the reagents comprise a combination of compounds for detecting one or more of leukocytes, glucose, urea, creatinine, and ammonia.
Clause 18. The device according to any one of Clauses 1 to 17, wherein each test component comprises one or more demarcated areas, each demarcated area comprising at least one reagent for detecting a respective substance.
Clause 19. The device according to Clause 18, each demarcated area further comprising:

an active area comprising the at least one reagent for detecting the respective substance; and an inactive area comprising colour reference data for comparing colour changes in the active area, wherein the inactive area is optionally divided into sub-areas according to activity levels of the respective substance.

Clause 20. A computer-implemented method for analysing spent peritoneal dialysate, the method comprising:

receiving image data of a set of test components, the image data comprising image test data for detecting one or more substances in the dialysate;

comparing the image test data against image reference data, the image test data representing reactions between the substances and one or more reagents comprised in the test components;

detecting the substances based on results of the comparison; and generating a message informative of the substances detected in the dialysate, wherein the image data optionally comprises the image reference data.

Devices for analysing spent peritoneal dialysate according to the present disclosure are thus disclosed herein. Various features, aspects, and advantages of the present disclosure will become more apparent from the following detailed description of the embodiments of the present disclosure, by way of non-limiting examples only, along with the accompanying drawings.

BRIEF DESCRIPTION OF THE DRAWINGS

FIG. 8 is a flowchart illustration of a method for analysing spent peritoneal dialysate.

DETAILED DESCRIPTION

Figure 1:
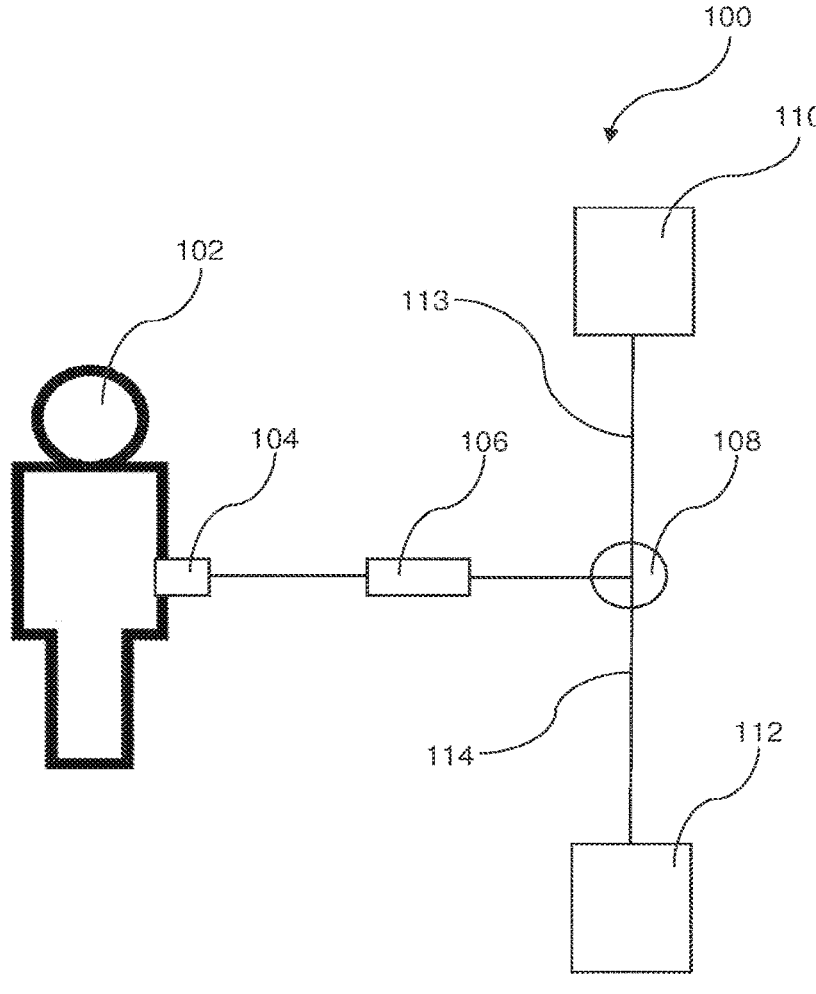
FIG. 1 is an illustration of a peritoneal dialysis apparatus.

For purposes of brevity and clarity, descriptions of embodiments of the present disclosure are directed to devices for analysing spent peritoneal dialysate, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognised by an individual having ordinary skill in the art, i.e. a skilled person, that the present disclosure may be practiced without specific details, and/or with multiple details arising from combinations of aspects of particular embodiments. In a number of instances, well-known systems, methods, procedures, and components have not been described in detail so as to not unnecessarily obscure aspects of the embodiments of the present disclosure.

In embodiments of the present disclosure, depiction of a given element or consideration or use of a particular element number in a particular figure or a reference thereto in corresponding descriptive material can encompass the same, an equivalent, or an analogous element or element number identified in another figure or descriptive material associated therewith.

References to "an embodiment/example", "another embodiment/example", "some embodiments/examples", "some other embodiments/examples", and so on, indicate that the embodiment(s)/example(s) so described may include a particular feature, structure, characteristic, property, element, or limitation, but that not every embodiment/example necessarily includes that particular feature, structure, characteristic, property, element or limitation. Furthermore, repeated use of the phrase "in an embodiment/example" or "in another embodiment/example" does not necessarily refer to the same embodiment/example.

The terms "comprising", "including", "having", and the like do not exclude the presence of other features/elements/steps than those listed in an embodiment. Recitation of certain features/elements/steps in mutually different embodiments does not indicate that a combination of these features/elements/steps cannot be used in an embodiment.

As used herein, the terms "a" and "an" are defined as one or more than one. The use of "/" in a figure or associated text is understood to mean "and/or" unless otherwise indicated. The term "set" is defined as a non-empty finite organisation of elements that mathematically exhibits a cardinality of at least one (e.g. a set as defined herein can correspond to a unit, singlet, or single-element set, or a multiple-element set), in accordance with known mathematical definitions. The terms "first", "second", "third", etc. are used merely as labels or identifiers and are not intended to impose numerical requirements on their associated terms.

In some representative or exemplary embodiments of the present disclosure, with reference to FIG. 2A to FIG. 2D, there is a test device 200 for analysing spent peritoneal dialysate from the peritoneal dialysis apparatus 100. The test device 200 includes a set of one or more housings 210 attachable to the peritoneal dialysis apparatus 100, a set of one or more test components 220 disposed in the housings 210, and a set of one or more fluidic conduits 230 connected to the housings 210 for communicating the dialysate from the peritoneal dialysis apparatus 100 to the housing 210. Each housing 210 may be referred to as a chamber 210 that accommodates a test component 220, such as by attaching the test component 220 to an inner surface of the chamber 210. Each test component 220 includes one or more reagents for detecting one or more substances, and the test components 220 are arranged for the reagents to react with the dialysate communicated to the chamber 210 and thereby detect the substances in the dialysate.

Figure 2A:
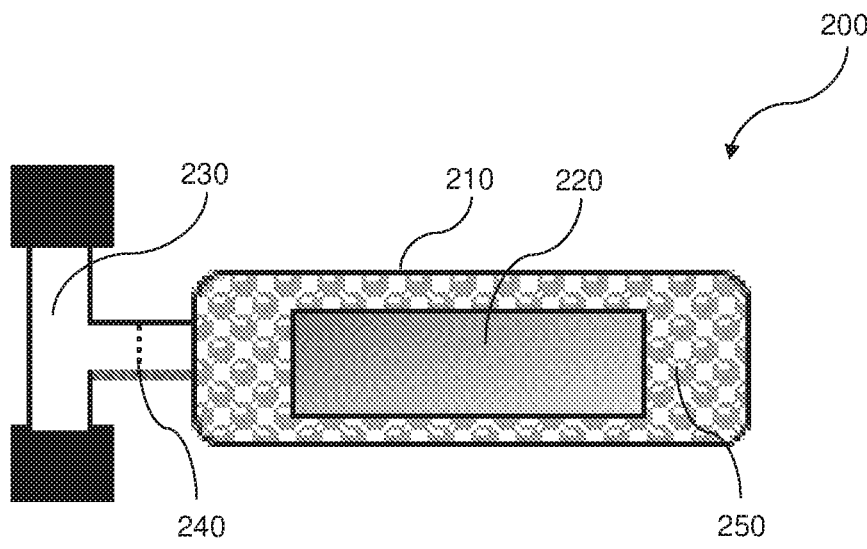
FIG. 2A to FIG. 2D are various illustrations of a test device for analysing spent peritoneal dialysate.
Figure 2B:
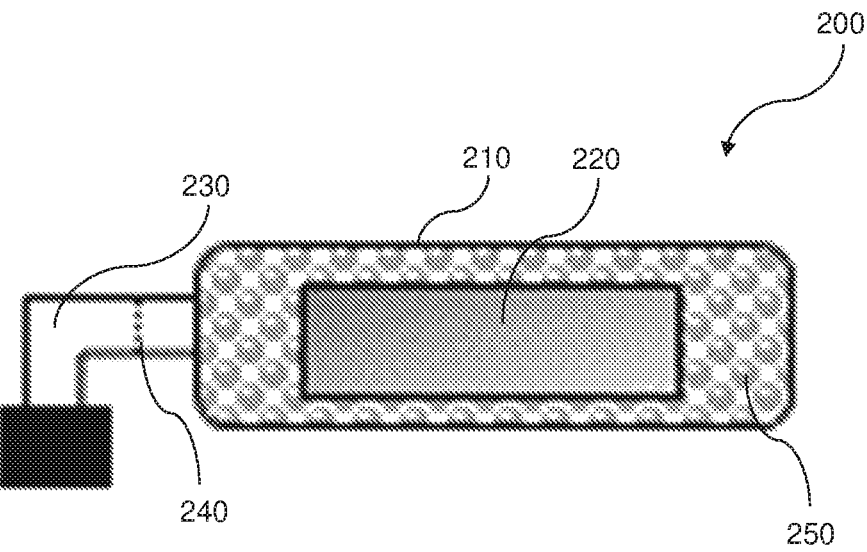
Figure 2C:
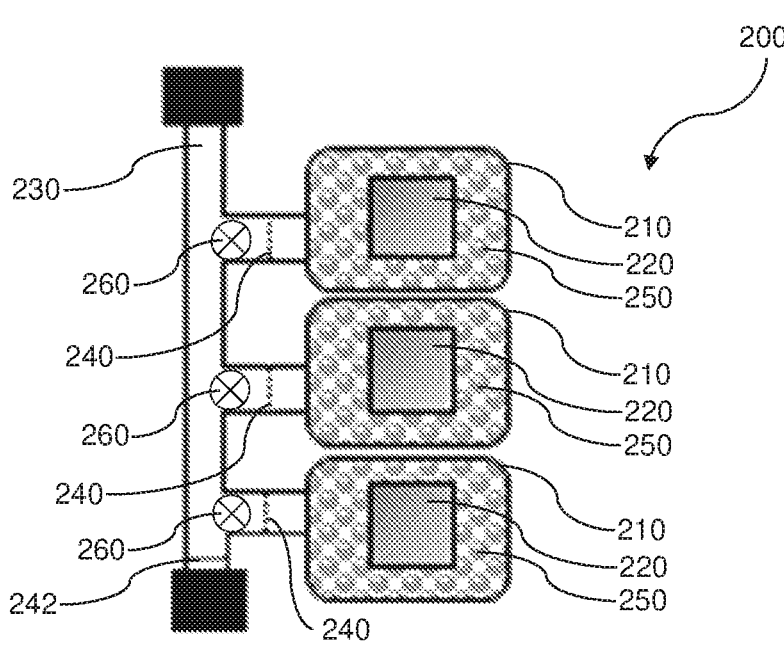
Figure 2D:
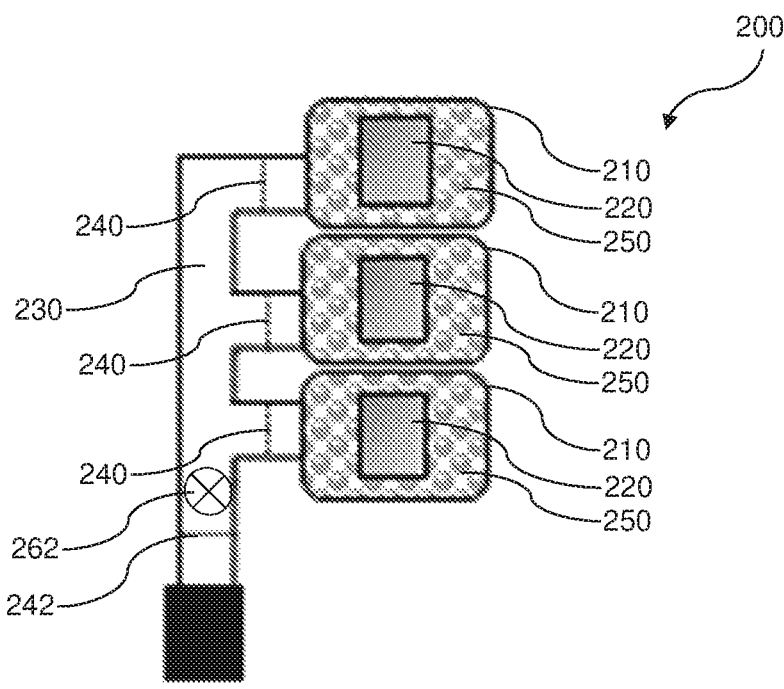

As shown in FIG. 2A and FIG. 2B, the test device 200 includes a chamber 210 and a test component 220 disposed in the chamber 210. A fluidic conduit 230 is connected to the chamber 210 for communicating the dialysate thereto for reacting with the reagents in the test component 220. As shown in FIG. 20 and FIG. 2D, the test device 200 includes a plurality of the chambers 210 and a plurality of the test components 220 disposed in the chambers 210. Particularly, each test component 220 is disposed in a respective one of the chambers 210. A plurality of fluidic conduits 230 are connected to the chambers 210 for communicating the dialysate thereto for reacting with the reagents in the test components 220.

Each fluidic conduit 230 is configured for regulating communication of the dialysate to the respective chamber 210. For example, the fluidic conduit 230 is narrower towards the chamber 210 to slow communication of the dialysate. The fluidic conduit 230 may have a larger opening leading to a constricted pathway that reduces the flow rate of the dialysate. The fluidic conduit 230 may include a semipermeable membrane for regulating communication of the dialysate to the chamber 210. Regulating the dialysate flow helps to optimise the flow rate and amount of dialysate that will enter the chamber 210 and contact the test component 220. A high dialysate flow rate will likely wash away the reagents on the test component 220 and conversely, a low dialysate flow will likely not allow the reactions to occur correctly. The fluidic conduit 230 may include a hydrophobic membrane that allows communication of gaseous substances, such as ammonia and carbon dioxide, to the chamber 210 to be detected by suitable reagents in the test component 220. For example, gaseous compounds with a high vapour pressure can be detected via a gas phase test strip.

The fluidic conduits 230 thus include a set of one or more semipermeable/hydrophobic membranes. In one embodiment, each of the fluidic conduits 230 includes a respective semipermeable hydrophobic membrane. In another embodiment, the fluidic conduits 230 include a common semipermeable/hydrophobic membrane. In yet another embodiment, the fluidic conduits 230 include both the common semipermeable/hydrophobic membrane and their respective semipermeable/hydrophobic membranes.

Instead of or in addition to the semipermeable or hydrophobic membrane, the fluidic conduit 230 may include a frangible seal 240 that fluidically isolates the chamber 210, wherein the frangible seal 240 is breakable to enable communication of the dialysate to the chamber 210. In other words, when the frangible seal 240 is intact, it blocks the fluidic conduit 230 and prevents the dialysate from flowing to the chamber 210. To initiate analysis of the dialysate, the patient 102 breaks the frangible seal 240 and opens the fluidic conduit 230, enabling the dialysate to flow to the chamber 210 and contact the test component 220 and react with the reagents.

The frangible seal 240 enables the controlled release of the dialysate from the fluidic conduit 230 to the chamber 210. The frangible seal 240 is formed such that its breaking strength or the force required to break it open is small enough for the patient 102, especially an elderly person. Conversely, the breaking strength should not be so small that the force of the dialysate flow can break the frangible seal 240. An example of the frangible seal 240 is a strip of frangible material that has weakened areas or zones of frangibility, such as perforations or score lines. The frangible strip can be broken along these weakened areas to open the fluidic conduit 230 and enable dialysate flow to the chamber 210. Another example of a frangible seal 240 is one that includes a frangible pin that fluidically seals when intact but can be broken to release the pin and open the seal. The released pin would remain in the fluidic conduit 230. It will be appreciated that there are other examples of frangible seals 240 that can be used in the test device 200.

The fluidic conduits 230 thus include a set of one or more frangible seals 240. In one embodiment, each of the fluidic conduits 230 includes a respective frangible seal 240. This gives the patient 102 control over test durations using the respective test components 220 in the respective housings 210. For example, the reagents of a first test component 220 may require a longer incubation time and the corresponding frangible seal 240 may be broken first. The corresponding frangible seal 240 for a second test component 220 that requires a shorter duration incubation time can be broken later. The incubation times can thus be coordinated by breaking the respective frangible seals 240 at appropriate times. In another embodiment, the fluidic conduits 230 include a common frangible seal 242. Once the common frangible seal 242 is broken, the dialysate will flow towards all the housings 210 and interact with all the test components 220. Such configuration may be preferred if the test components 220 have similar incubation times and breaking a single common frangible seal 242 is easier, especially for elderly patients. In yet another embodiment as shown in FIG. 2C and FIG. 2D, the fluidic conduits 230 include both the common frangible seal 242 and their respective frangible seals 240.

The test device 200 may further include a set of one or more mesh components 250 disposed in the chambers 210 for regulated wetting of the test components 220 by the dialysate. For example as shown in FIG. 2A and FIG. 2B, the test component 220 is encased within or disposed on the mesh component 250 so that when the dialysate enters the chamber 210, the mesh component 250 allows the test component 220 to be slowly wetted by the dialysate. Geometrical properties of the mesh component 250, such as size of the holes, control or regulate the wetting rate. The mesh component 250 may be porous-like, such as one that is formed of a sponge-like material. The mesh component 250 may further act as a carrier layer for supporting the test component 220 housed in the chamber 210. The mesh component 250 can be used in cooperation with the fluidic conduit 230, semipermeable membrane, hydrophobic membrane, and/or frangible seal 240 to optimise the flow rate and amount of dialysate that contacts the test component 220.

In one embodiment as shown in FIG. 2A, the fluidic conduit 230 has a three-way connector, such as a T-shaped or Y-shaped connector. The test device 200 is attachable to a drain bag 112 of the peritoneal dialysis apparatus 100. More specifically, the chamber 210 is attachable to the peritoneal dialysis apparatus 100 by connecting the three-way fluidic conduit 230 to the drain bag 112 which is used for collecting the dialysate discharged from the peritoneal dialysis apparatus 100. The first end of the three-way fluidic conduit 230 is connected to an inlet 116 of the drain bag 112 and the second end is connected to the drain tubing 114. Each of the first and second ends includes suitable fluidic couplers for easy connection/disconnection and for sealing the fluidic conduit 230 when the test device 200 is detached. The third end leads to the chamber 210 and the frangible seal 240 may be disposed near the third end.

In one embodiment as shown in FIG. 2B, the fluidic conduit 230 has a two-way connector, such as a L-shaped connector. The chamber 210 is attachable to the peritoneal dialysis apparatus 100 by connecting the two-way fluidic conduit 230 to the drain bag 112 which is used for collecting the dialysate discharged from the peritoneal dialysis apparatus 100. The first end of the two-way fluidic conduit 230 is connected to the inlet 116 of the drain bag 112. The first end includes a suitable fluidic coupler for easy connection/ disconnection and for sealing the fluidic conduit 230 when the test device 200 is detached. The second end leads to the chamber 210 and the frangible seal 240 may be disposed near the second end.

Figure 2E:
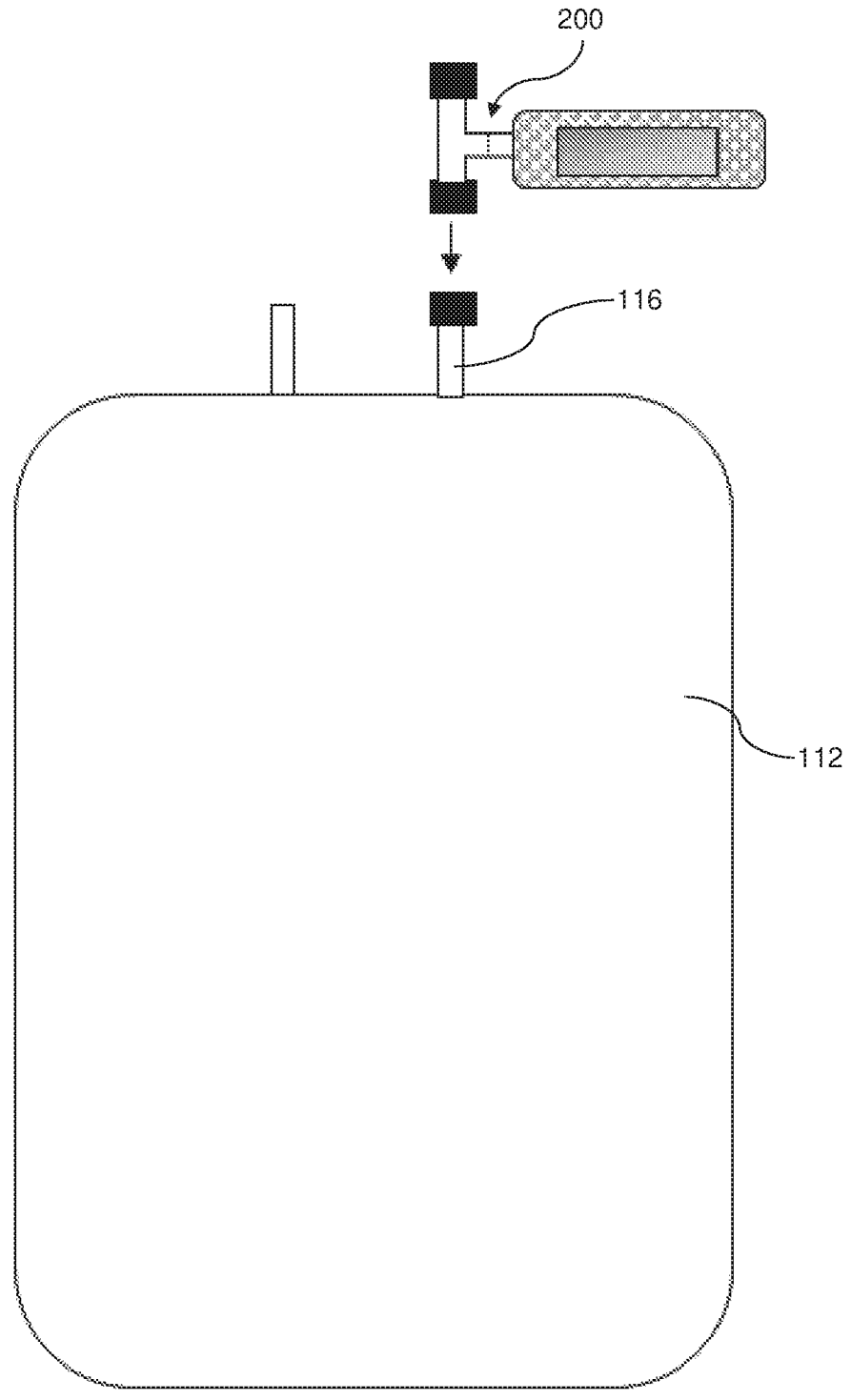
FIG. 2E to FIG. 2H are various illustrations of the test device of FIG. 2A to FIG. 2D attached to the peritoneal dialysis apparatus.
Figure 2F:
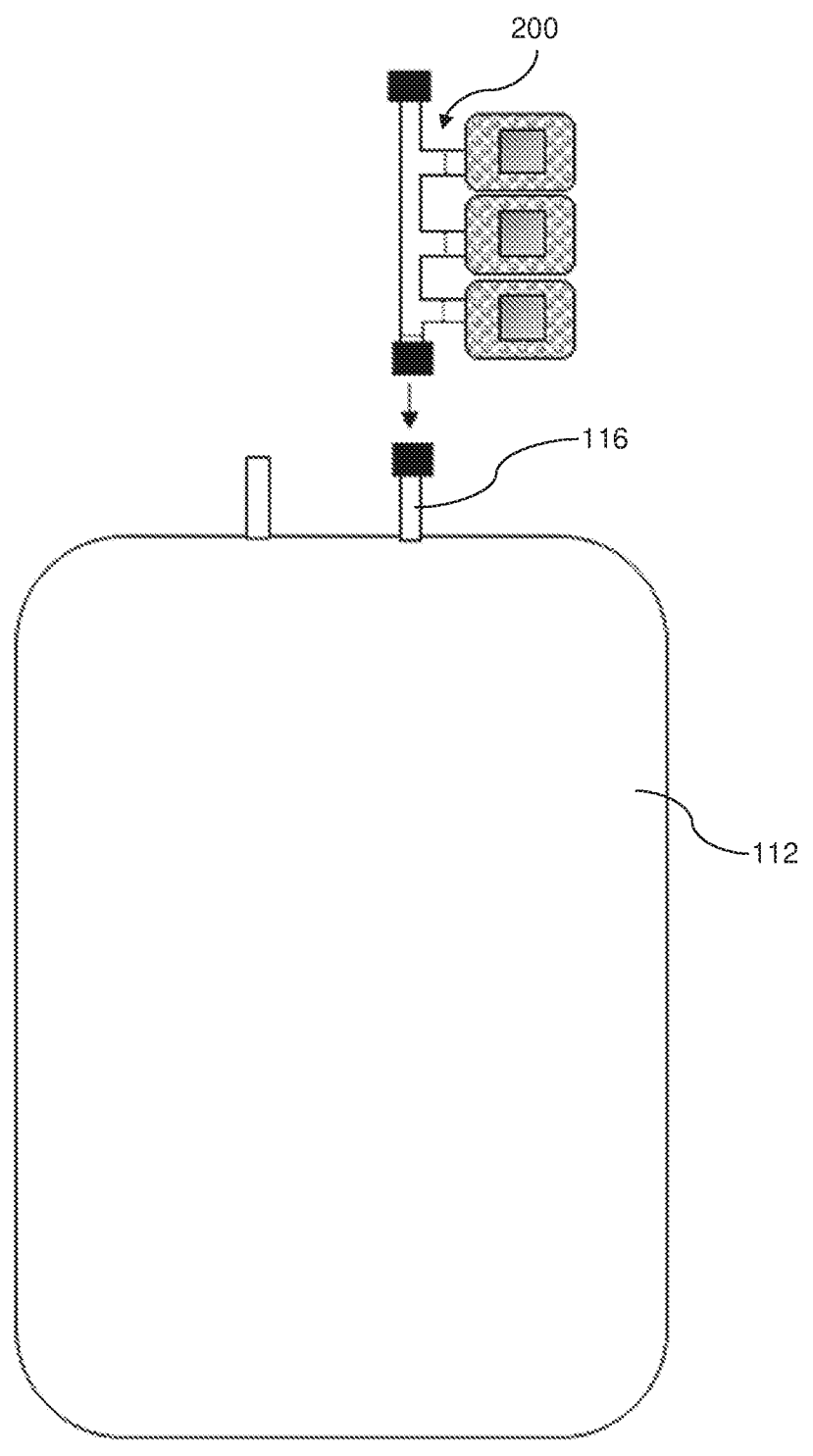
Figure 2G:
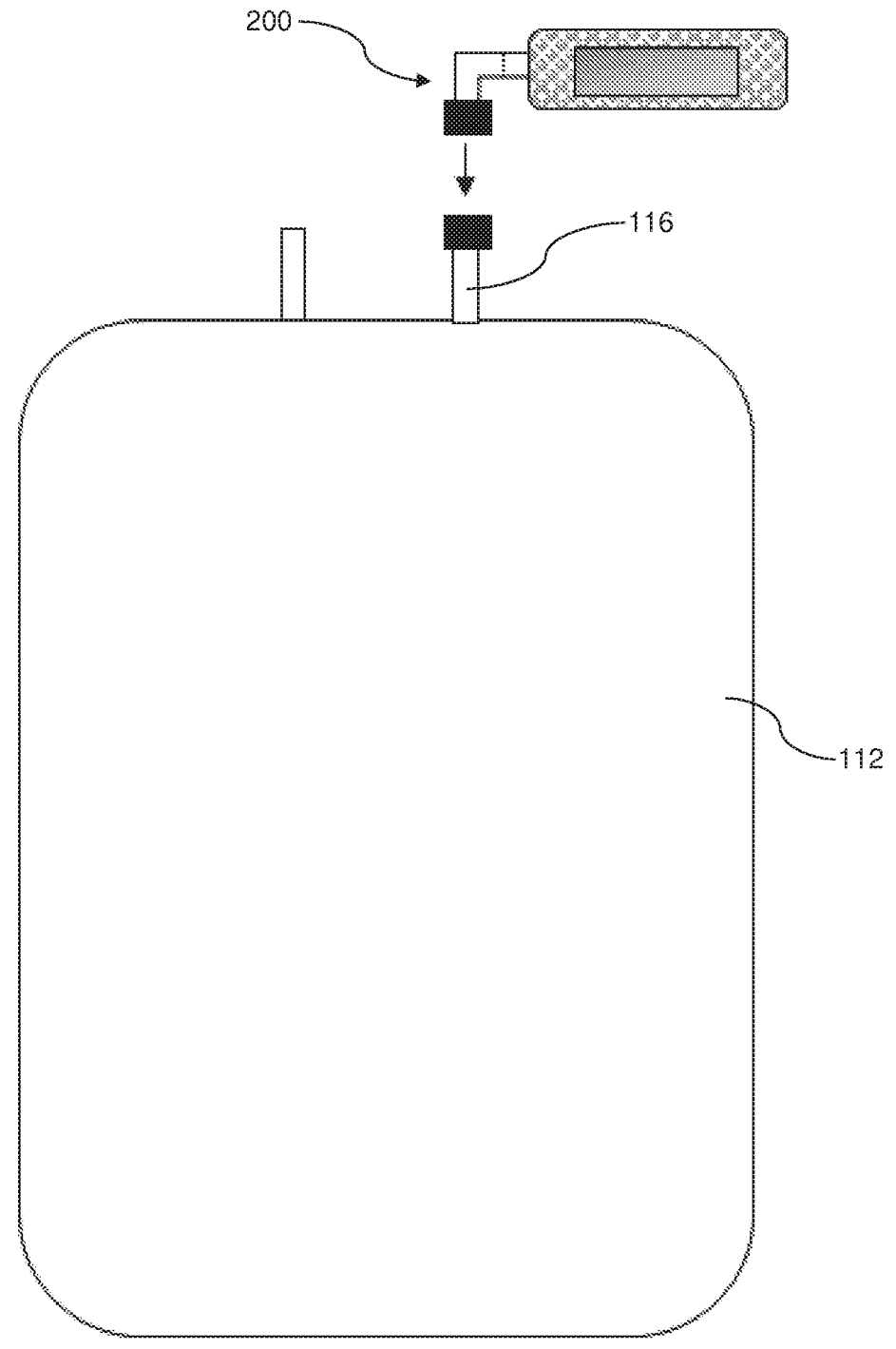
Figure 2H:
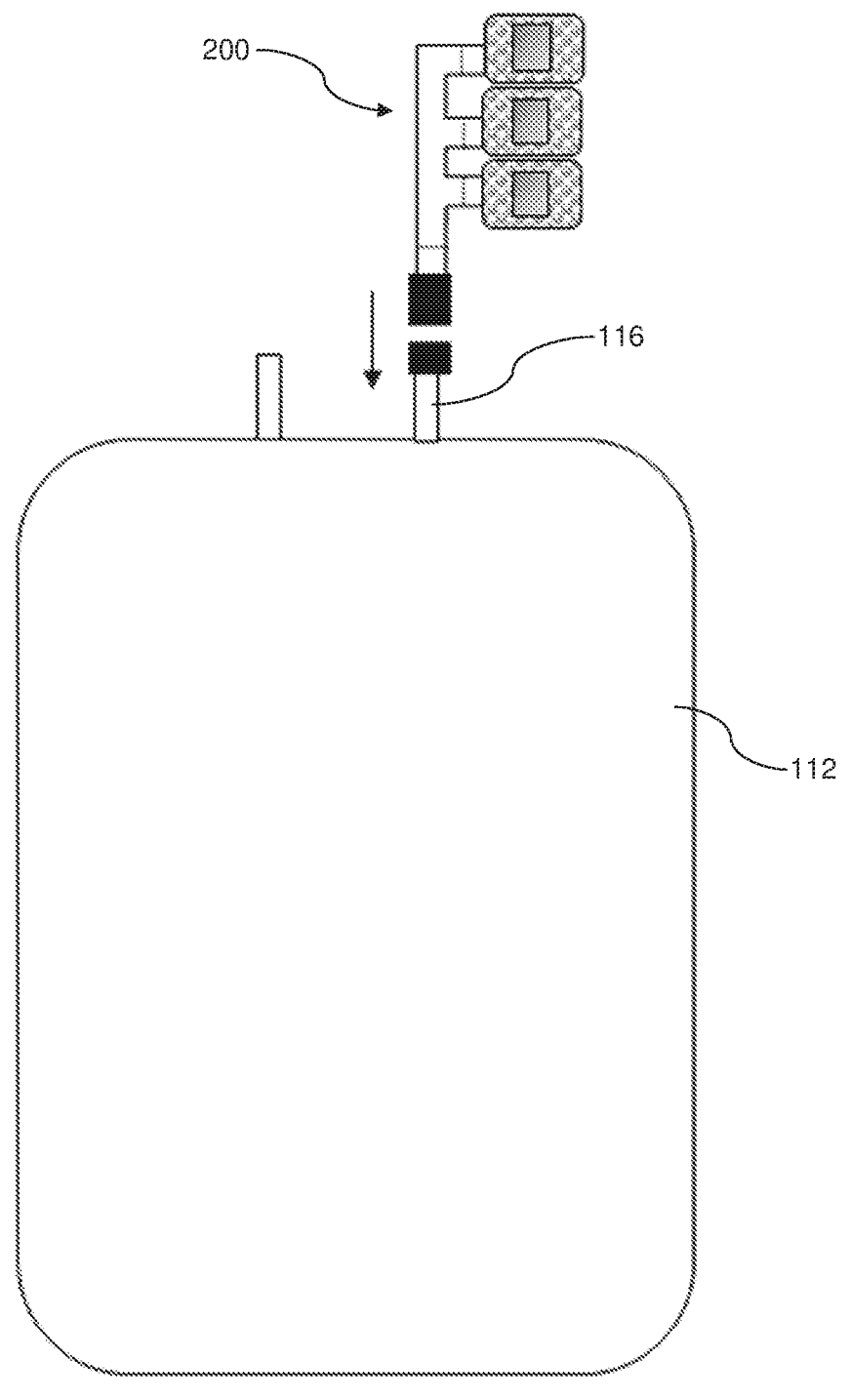

In some embodiments as shown in FIG. 2E and FIG. 2F, the test device 200 is attached to the drain bag 112 and drain tubing 114 before commencing peritoneal dialysis. After peritoneal dialysis and collection of the dialysate in the drain bag 112, the drain bag 112 and the test device 200 attached thereto are disconnected from the drain tubing 114. In some embodiments as shown in FIG. 2G and FIG. 2H, the test device 200 is attached to the drain bag 112 after peritoneal dialysis and collection of the dialysate in the drain bag 112.

In the embodiments as shown in FIG. 2E to FIG. 2H, the test device 200 is connected to and in fluid communication with the drain bag 112. The drain bag 112 and test device 200 are positioned to allow the dialysate to flow from the drain bag 112 to the fluidic conduit 230. The frangible seal 240 is then broken to transfer the dialysate from the fluidic conduit 230 to the chamber 210. However, the sudden gush of dialysate may wash out the reagents in the test component 220. To mitigate this, the test device 200 may include a valve mechanism for selectively controlling communication of the dialysate to the chamber 210. The patient 102 or user operates the valve mechanism to switch on/off the dialysate flow to the chamber 210 as well as to control the dialysate flow rate, allowing the dialysate to flow slowly to the chamber 210. In one example, the valve mechanism is selectable between an open state and a closed state to enable and disable, respectively, communication of the dialysate to the chamber 210. In another example, the valve mechanism is further configured for finer selections to allow control of the flow rate of the dialysate. The valve mechanism may include one or more of any suitable valve known to the skilled person, such as but not limited to ball valve, needle valve, plug valve, global valve, butterfly valve, poppet valve, and the like. Use of the valve mechanism also helps to control the incubation time between the reagents and the dialysate. The dialysate in the chamber 210 contacts the test component 220 and reacts with the reagents to detect substances in the dialysate.

As shown in FIG. 2O and FIG. 2D, the valve mechanism may include a set of one or more valves 260. In one embodiment as shown in FIG. 2O, a respective valve 260 is disposed in each of the fluidic conduits 230. In another embodiment as shown in FIG. 2D, the fluidic conduits 230 share a common valve 262. In yet another embodiment, the valve mechanism includes both the common valve 262 and the valves 260 for the respective fluidic conduits 230. Similar to the frangible seals 240,242 described above, the arrangement of the valves 260,262 can allow the patient 102 to exercise greater control over testing of the dialysate using the test components 220 in the respective housings 210. The valves 260,262 may be disposed in the fluidic conduits 230 before or after the frangible seals 240,242.

Depending on the incubation time required, the test device 200 may be repositioned to allow flowback of the dialysate from the chamber 210 to the fluidic conduit 230. Prolonged exposure of the reagents to the dialysate can leach chemicals from the reagents and compromise results of the reactions. For example, the semipermeable membranes or broken frangible seals 240 allow such flowback to occur. Notable, if the valve mechanism is present, the flowback will only occur if the valve mechanism is selected to the open state. Particularly, the valves 260,262 of the valve mechanism are bi-directional that allow flow towards the housings 210 as well as flowback.

Instead of the drain bag 112, the chamber 210 may be attached to the peritoneal dialysis apparatus 100 to receive the dialysate by connecting the fluidic conduit 230 to other parts of the peritoneal dialysis apparatus 100. In one example, the fluidic conduit 230 can be connected to the drain tubing 114 for discharging the dialysate but may not be connected to the drain bag 112. In another example, the fluidic conduit 230 can be connected to the transfer set tubing 106 which is used to connect to the catheter 104. It will be appreciated that operations of the test device 200 to receive the dialysate using the transfer set tubing 106 or drain tubing 114 are similar to those for the drain bag 112.

Figure 3A:
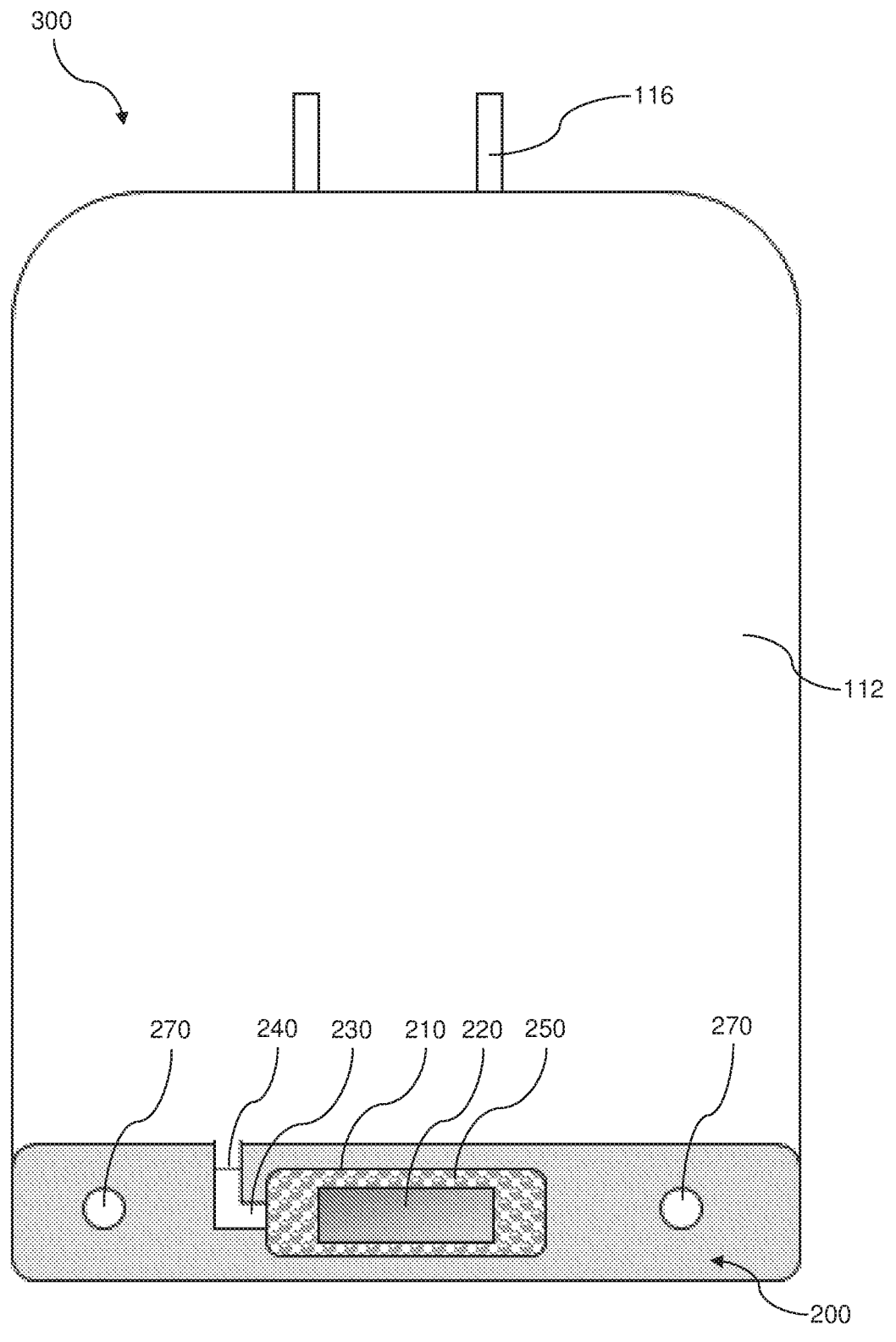
FIG. 3A and FIG. 3B are various illustrations of a test device attached inside a drain bag of the peritoneal dialysis apparatus.
Figure 3B:
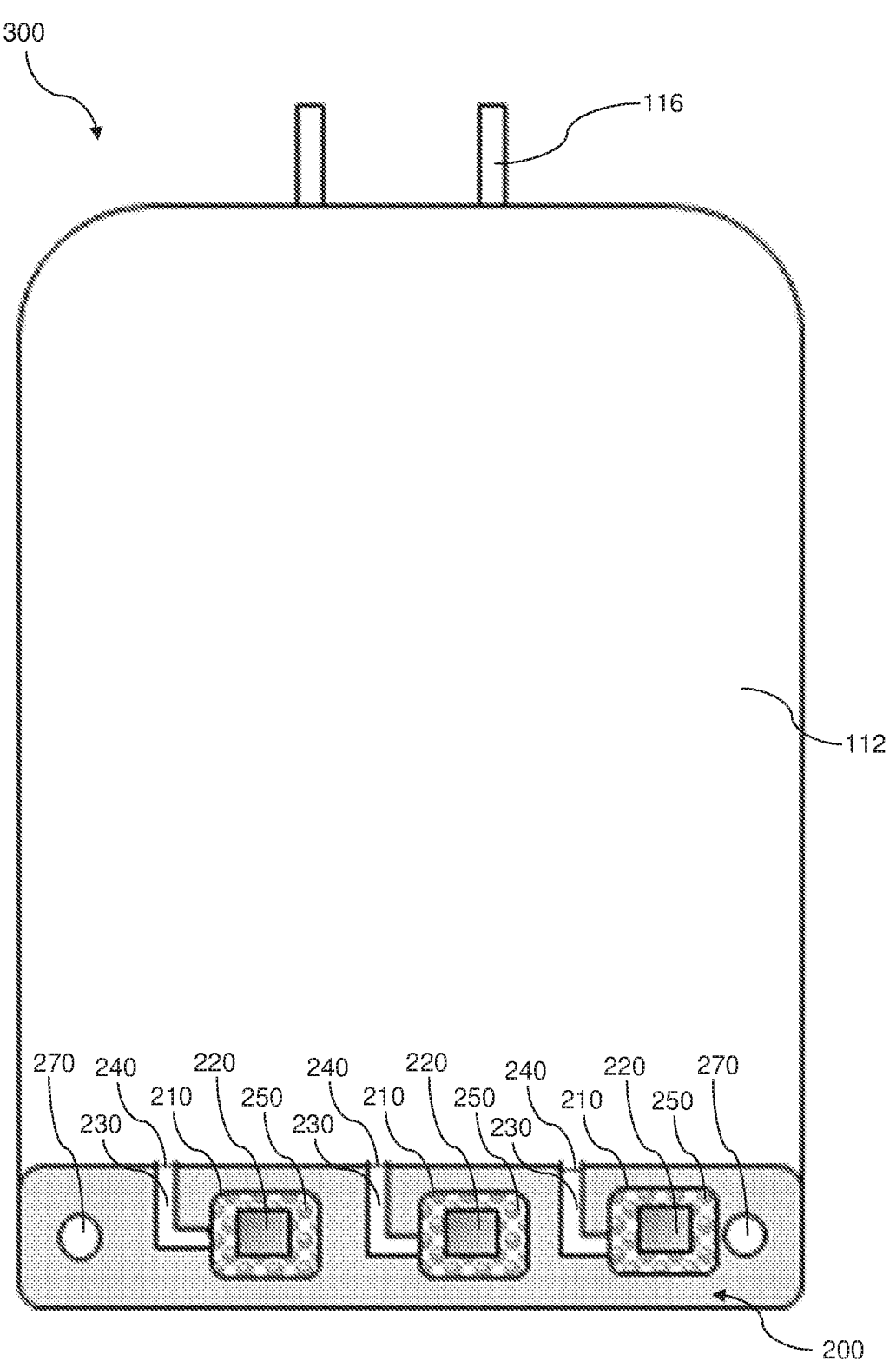

In some embodiments, the set of chambers 210 is attachable inside the drain bag 112 and the set of fluidic conduits 230 is arranged for communicating the dialysate from the drain bag 112 to the chambers 210. In one embodiment with reference to FIG. 3A, there is a bag device 300 having the test device 200 integrated therein. The bag device 300 includes the drain bag 112 and test device 200 which is attached inside the drain bag 112. The test device 200 includes a chamber 210, a test component 220, and a fluidic conduit 230 for communicating the dialysate to the chamber 210. In another embodiment with reference to FIG. 3B, the test device 200 includes a plurality of the chambers 210, a plurality of the test components 220, and a plurality of the fluidic conduits 230 for communicating the dialysate to the chambers 210. The test device 200 may be attached to the inside of the drain bag 112 by various means such as but not limited to ultrasonic welding, heat sealing, and adhesives. The test device 200 may be positioned near the bottom edge of the drain bag 112 to receive the dialysate more easily.

During peritoneal dialysis, the drain bag 112 collects the dialysate via the drain tubing 114 and inlet 116 but the frangible seal 240 prevents the dialysate from flowing to the chamber 210. During or after peritoneal dialysis, for each chamber 210 of the test device 200, the frangible seal 240 is broken to transfer the dialysate from the fluidic conduit 230 to the chamber 210. The test device 200 may be repositioned to allow flowback of the dialysate from the chamber 210 to drain bag 112 via the fluidic conduit 230. For example, the test device 200 may include holes 270 for inverting and carrying the drain bag 112 and test device 200 on a support structure to facilitate the flowback.

Figure 4A:
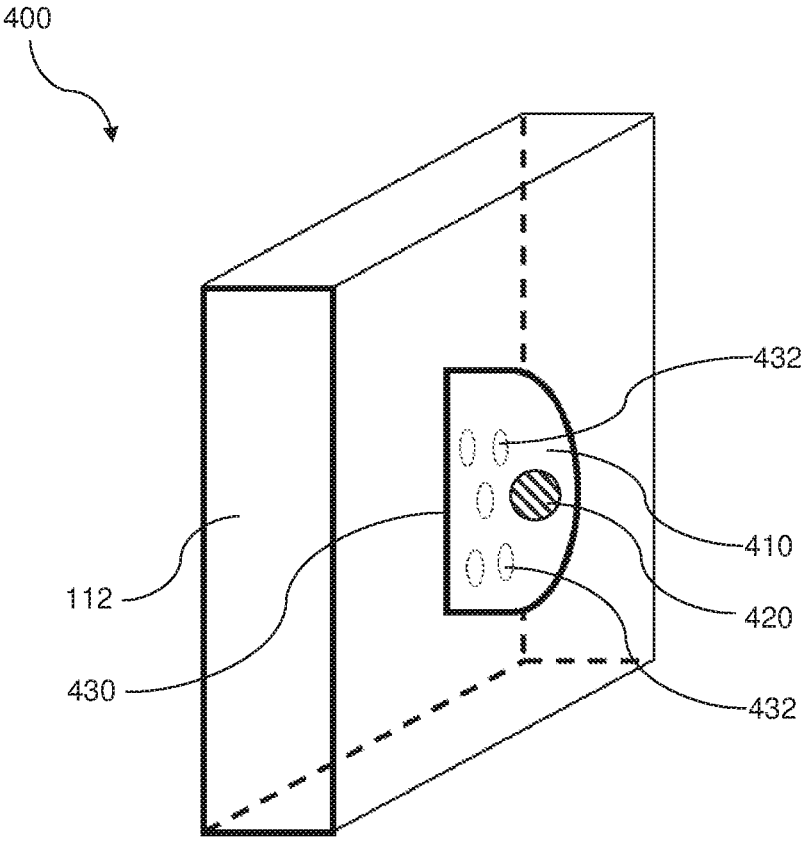
FIG. 4A and FIG. 4B are various illustrations of a bag device for analysing spent peritoneal dialysate.
Figure 4B:
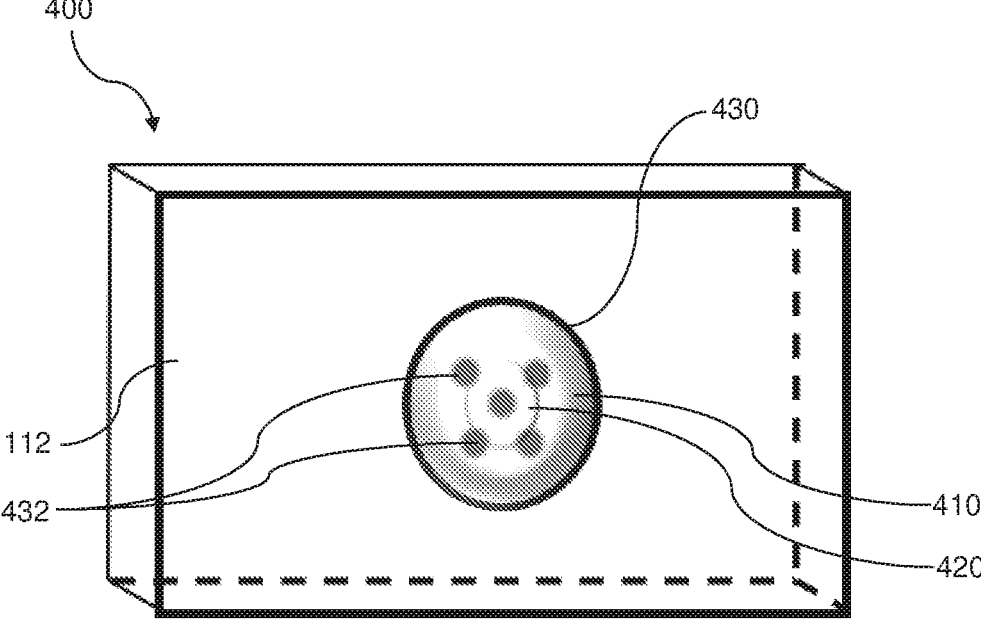

In some representative or exemplary embodiments of the present disclosure, with reference to FIG. 4A and FIG. 4B, there is a bag device 400 for analysing spent peritoneal dialysate from the peritoneal dialysis apparatus 100. The bag device 400 includes a set of one or more housings 410 attachable to the peritoneal dialysis apparatus 100, a set of one or more test components 420 disposed in the housings 410, and a set of one or more fluidic conduits 430 connected to the housings 410 for communicating the dialysate from the peritoneal dialysis apparatus 100 to the housings 410. Each housing 410 may be referred to as a compartment 410 that accommodates a test component 420. The test component 420 includes reagents that react with the dialysate communicated to the compartment 410 and thereby detect substances in the dialysate.

As shown in FIG. 4A and FIG. 4B, the bag device 400 includes a compartment 410, a test component 420 disposed in the compartment 410, and a fluidic conduit 430 connected to the compartment 410. However, it will be appreciated that the bag device 400 may include a plurality of the same, allowing for multiple compartments 410 housing multiple test components 420 to be attached to the peritoneal dialysis apparatus 100.

The bag device 400 further includes a drain bag 112 attachable to the peritoneal dialysis apparatus 100 for collecting the dialysate discharged therefrom. The drain bag 112 is formed of a flexible material such as flexible polyvinyl chloride (PVC). The compartment 410 is attached to an outer surface of the drain bag 112 such that the compartment 410 protrudes out of the drain bag 112. The fluidic conduit 430 is formed on the outer surface of the drain bag 112 for communicating the dialysate from the drain bag 112 to the compartment 410 through the outer surface of the drain bag 112. The compartment 410 can be attached to the outer surface of the drain bag 112 using suitable bonding means, such as ultrasonic welding, heat sealing, and adhesives. Additionally, the periphery of the compartment 410 is sealed against the outer surface of the drain bag 112 such that the fluidic conduit 430 is the only mode of fluid communication from the drain bag 112 to the compartment 410 where the test component 420 is stored. The test component 420 is attached to an inner surface of the compartment 410 by various means as described above.

In one embodiment, the fluidic conduit 430 includes a perforated area which is an area that has one or more perforations 432 formed through the outer surface of the drain bag 112. The perforations 432 are designed to optimise the flow rate and amount of dialysate that will enter the compartment 410 and contact the test component 420. A high dialysate flow rate will likely wash away the reagents on the test component 420 and conversely, a low dialysate flow will likely not allow the reactions to occur correctly.

Figure 5A:
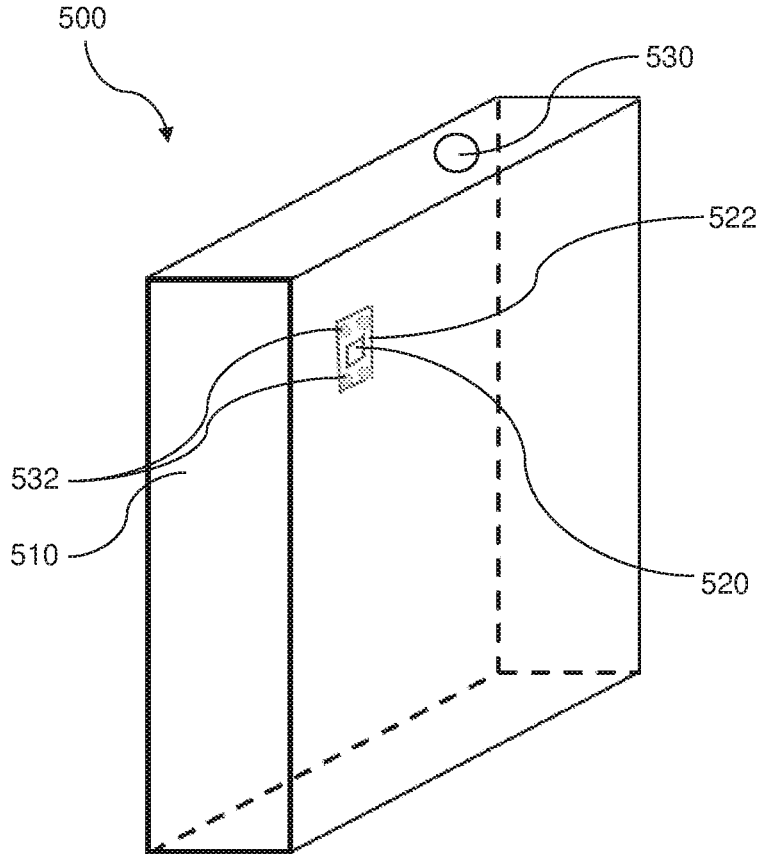
FIG. 5A and FIG. 5B are various illustrations of another bag device for analysing spent peritoneal dialysate.
Figure 5B:
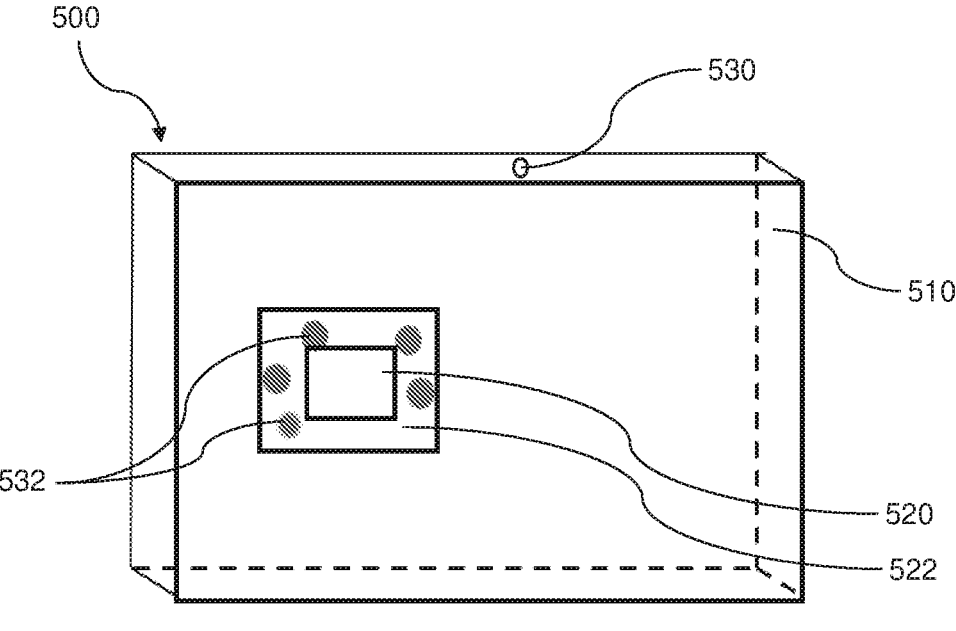

In some representative or exemplary embodiments of the present disclosure, with reference to FIG. 5A and FIG. 5B, there is a bag device 500 for analysing spent peritoneal dialysate from the peritoneal dialysis apparatus 100. The bag device 500 includes a single housing 510 attachable to the peritoneal dialysis apparatus 100 and a set of one or more test components 520 disposed in the housing 510. The housing 510 is or includes a drain bag 112 for collecting the discharged dialysate, and the housing 510 may be referred to as the drain bag 510 that accommodates the test components 520. Each test component 520 includes reagents that react with the dialysate communicated to the drain bag 510 and thereby detect substances in the dialysate. The bag device 500 further includes a fluidic conduit 530 connected to the drain bag 510 for communicating the dialysate from the peritoneal dialysis apparatus 100 to the drain bag 510. For example, the fluidic conduit 530 is an inlet of the drain bag 510 that connects to the drain tubing 114.

As shown in FIG. 5A and FIG. 5B, the bag device 500 includes a drain bag 510, a test component 520 disposed in the drain bag 510, and a fluidic conduit 430 connected to the drain bag 510. However, it will be appreciated that the bag device 500 may include a plurality of the test components 520, allowing for the drain bag 510 housing multiple test components 520 to be attached to the peritoneal dialysis apparatus 100.

The test component 520 is attached to an inner surface of the drain bag 510 using suitable bonding means, such as ultrasonic welding, heat sealing, and adhesives. In one embodiment, the bag device 500 further includes a set of one or more inner layers 522 attached to the inner surface of the drain bag 510 and covering the test components 520. Each inner layer 522 is arranged to cover a respective one of the test components 520. The inner layer 522 may be attached using similar bonding means and helps to make the test component 520 stay in place inside the drain bag 510. Moreover, the inner layer 522 regulates the dialysate flow and helps to optimise the flow rate and amount of dialysate that will contact the test component 520.

In one embodiment, the inner layer 522 is impermeable but the periphery of the inner layer 522 is not completely sealed against the inner surface of the drain bag 510. Particularly, gaps are formed at the periphery to enable some fluid flow to the test component 520. In another embodiment, the inner layer 522 includes a semipermeable membrane for regulating communication of the dialysate to the test component 520. The periphery of the inner layer 522 is sealed against the inner surface of the drain bag 112 such that the semipermeable membrane is the only mode of fluid communication to the test component 520. In one example, the semipermeable membrane may be formed of a material that is structurally or inherently semipermeable. In another example, the inner layer 522 includes a perforated area which is an area that has one or more perforations 532 that form the semipermeable membrane. It will be appreciated that these perforations 532 may be similar to the perforations 432 described above.

As described above, the housing 510 is or includes the drain bag 112 which accommodates the test component 520. The test component 520 may be attached to other parts of the peritoneal dialysis apparatus 100 instead of the drain bag 112. In one example, the housing 510 is or includes the transfer set tubing 106 and the test component 520 is attached to an inner surface of the transfer set tubing 106. In another example, the housing 510 is or includes the drain tubing 114 and the test component 520 is attached to an inner surface of the drain tubing 114.

In some embodiments, the test component 520 is disposed in the housing 510, such as the drain bag 112, transfer set tubing 106, or drain tubing 114, by depositing the reagents on the inner surface of the housing 510. The reagent deposition may be in the form of a coating on the entire inner surface or a part thereof.

Figure 6A:
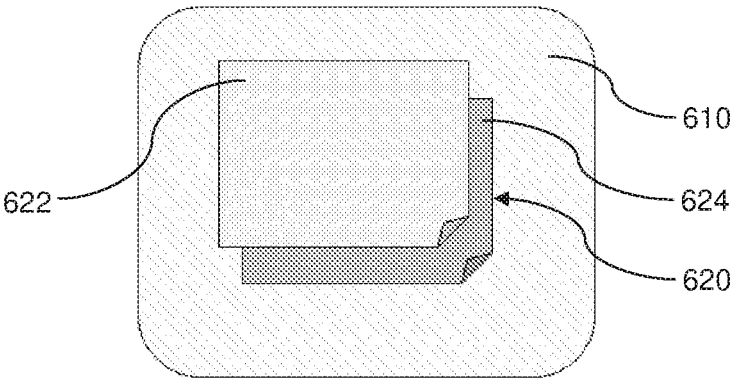
FIG. 6A and FIG. 6B are various illustrations of a test component attached to a surface.

With reference to FIG. 6A, there is an exemplary test component 620 similar or analogous to the test components 220/420/520 described above. The test component 620 is attached to a surface 610 such as the inner surface of the drain bag 112, transfer set tubing 106, or drain tubing 114. An inner layer 622 such as having the semipermeable membrane is attached to the surface 610 and covers the test component 620. The test component 620 includes a number of layers including a reagent layer or pad 624 that holds the reagents for detecting the substances. The reactions between the reagents and the substances may be read on either side of the test component 620 through the inner layer 622 or the surface 610 which is transparent.

Figure 6B:
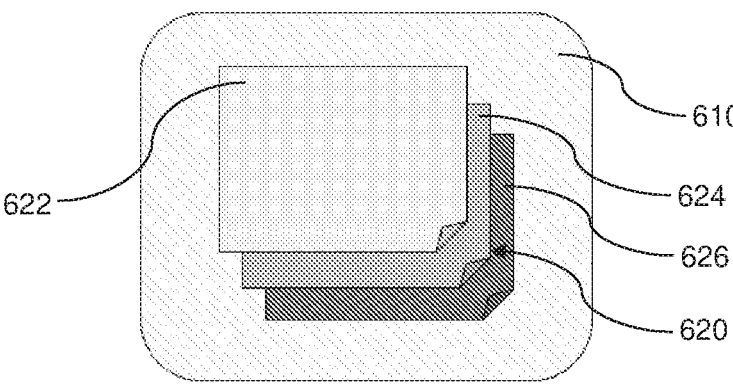

In one embodiment, the test component 620 is integrated with the surface 610 and may be directly attached to the surface 610 using an adhesive or by printing on the surface 610. In another embodiment as shown in FIG. 6B, the test component 620 is a standalone component that can function independently without being attached to the surface 610. The test component 620 includes an additional carrier or support layer 626 that is attached to the surface 610 and holds the test component 620 in place on the surface 610. The carrier layer 626 may be formed using a paper, membrane, or polymer with various fluidic properties. The reactions between the reagents and the substances may be read on only one side of the test component 620 through the inner layer 622. It will be appreciated that the test component 620 may include other layers such as but not limited to a mesh layer, an indicator layer, an iodate layer, an absorbent layer, a compensation layer, a spreader layer, and a separator layer.

The reagents are in the form of dry reagents that may include compounds such as indicator dyes, metals, enzymes, polymers, antibodies, and various other chemicals that are dried on the reagent layer 624. The reagent layer 624 may be a porous substrate such as one made of paper/cellulose, wherein the reactants are absorbed directly into the porous substrate. Alternatively, the reagent layer 624 may be a plastic mesh that is impregnated with the reagents. The reagent layer 624 may have an array of one or more demarcated areas such that each demarcated area has at least one reagent for detecting a respective substance in the dialysate.

Upon contact with the dialysate, the reagents react with the substances in the dialysate and change colour. The reagents may be qualitative such that the colour change only determines if the dialysate is positive or negative, i.e. whether a substance is present or absent. Preferably, the reagents are semiquantitative such that intensity of the colour changes are proportional or correspond to the activity level or concentration of the substances in the dialysate. This provides a more quantitative analysis of the dialysate which will be useful in diagnosing conditions or infections such as peritonitis.

The reagents include a combination of chemical compounds for detecting one or more of substances in the dialysate. These substances may be referred to as waste compounds or waste products, and non-limiting examples of these substances include leukocytes, glucose, urea, creatinine, and ammonia. The reagents may also detect the pH value of the dialysate to evaluate its acidity/alkalinity.

The reagents may include an indoxyl ester compound and a chromogen such as a diazonium salt for leukocyte measurement. The indoxyl ester compound will be hydrolysed with the presence of esterase from granulocytic leukocytes in the dialysate. This hydrolysis reaction will turn indoxyl ester compound to yield indoxyl which will react with the diazonium salt to produce a characteristic purple colour. Leukocyte esterase activity in peritoneal dialysis increases when leukocyte counts in the dialysate increase in response to peritoneal infections such as peritonitis. Using the reagents to measure leukocytes esterase has been shown to be effective in rapidly and accurately diagnosing spontaneous bacterial peritonitis, and one study has shown the diagnostic accuracy to be approximately 96.1%. Since the reagents respond to different activity or concentration levels of leukocyte esterase which is proportional to the amount of leukocytes in the dialysate, the colour changes or responses of the reagents can be used to differentiate negative, trace, small, and large quantity of leukocyte presence.

The reagents may include glucose oxidase, peroxidase, and a chromogen such as potassium iodide for glucose measurement. Glucose measurement is based on a double sequential enzyme reaction. The first enzyme glucose oxidase catalyses the formation of gluconic acid and hydrogen peroxide from the oxidation of glucose. The second enzyme peroxidase then catalyses the reaction of hydrogen peroxide with the chromogen potassium iodide to oxidize the chromogen to a range of colours. For example, the colours may range from blue-green, greenish-brown, brown, to dark brown. To achieve this double sequential enzyme reaction, the reagents are arranged in a multi-layer arrangement in the test component 620.

The reagents may include urease and a suitable chromogen for urea measurement. Urea measurement is based on urease catalysed conversion of urea to ammonia and carbon dioxide. The pH value of the reaction medium is monitored by the chromogen and the intensity of the product colour is proportional to the urea concentration in the dialysate. Similar to glucose measurement, the reagents for urea measurement are arranged in a multi-layer arrangement in the test component 620 so that the reactions can happen sequentially.

Some reagents are suitable for repeated measurements during peritoneal dialysis. Certain reagent strips are able to maintain reactivity between dialysate exchanges and return a new reading during the next cycle. Examples of such reagents that can be reused repeatedly are suitable for measuring pH values and detecting ammonia. On the other hand, some reagents are for single use only as their colour changes due to reactions with the substances are non-reversible. These reagents only allow for detection of the substances once per peritoneal dialysis therapy, such as testing for these substances after the therapy. These substances include glucose, urea, and creatinine.

Figure 7A:
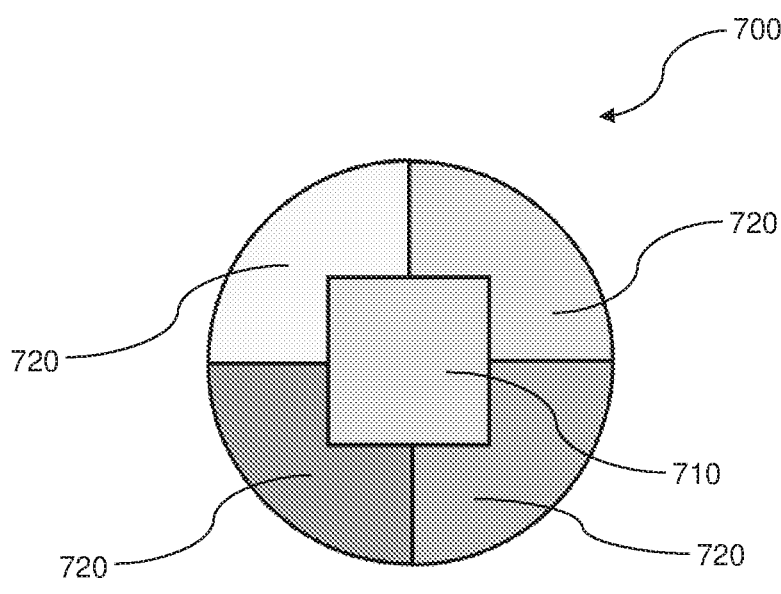
FIG. 7A and FIG. 7B are various illustrations of a demarcated area of the test component.
Figure 7B:
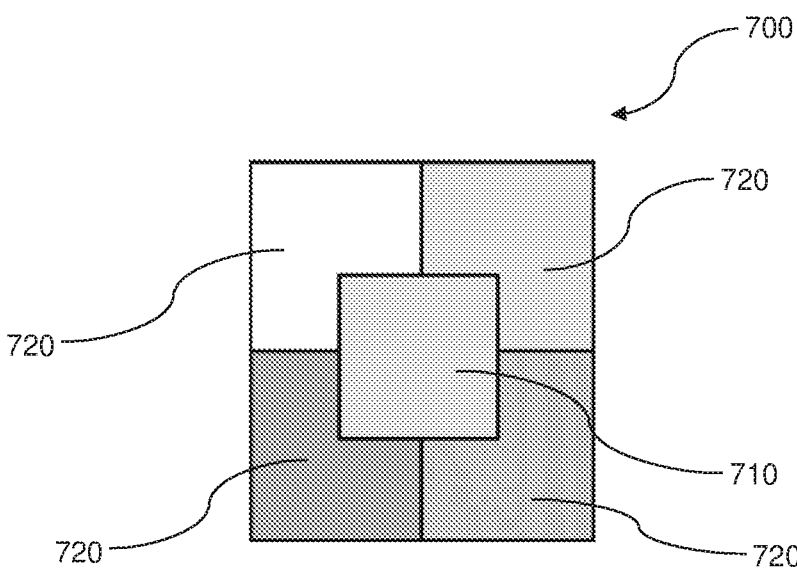

As described above, the test component 620 may have one or more demarcated areas each having at least one reagent for detecting a respective substance. With reference to FIG. 7A and FIG. 7B, each demarcated area 700 may include an active area 710 and an inactive area 720. The active area 710 contains the at least one reagent for detecting the respective substance. The reactions between the reagent and the substance will cause the active area 710 to change colour, allowing the patient 102 (or other user such as a clinician) to detect whether the substance is present in the dialysate. Moreover, the intensity of the colour change may allow the patient 102 or user to determine the concentration of the substance. The inactive area 720 contains colour reference data for comparing colour changes in the active area 710. Particularly, the colour change of the reagent in the active area 710 is compared against the colour reference data which present a visual chromatic chart for determining the presence and/or concentration of the respective substance. The inactive area 720 may be divided into sub-areas according to activity or concentration levels of the respective substance.

Arranging the active area 710 and inactive area 720 together on the demarcated area 700 facilitates comparison of the reagent colour change (image or colour test data) against the chromatic chart (image or colour reference data). Viewing the image test data and image reference data in the same visual field prevents ambient light influence which could result in reading the image test data wrongly. For example, if the image test data is viewed solely, the colour change may be influenced by ambient light variation and the patient 102 may interpret a different colour, potentially resulting in inaccurate diagnosis. The concentration range of the substance can be determined based on the sub-area of the inactive area 720 that has the closest image reference data to the image test data.

One exemplary arrangement of the active area 710 and inactive area 720 is shown in FIG. 7A. The active area 710 is arranged in a middle circle and the inactive area 720 is divided into four sub-areas or quadrants surrounding the active area 710. Another exemplary arrangement of is shown in FIG. 7B wherein the active area 710 is arranged in a middle rectangle and the inactive area 720 is divided into four rectangles surrounding the active area 710. Each division or sub-area of the inactive area 720 represents a concentration range of the respective substance.

The patient 102 may interpret the reaction results on the test component 620 himself/herself or may instead use an electronic device to read the reaction results. The electronic device may be a dedicated reader device provided for analysing the dialysate or an electronic device of the patient 102, such as a mobile phone or computer. The electronic device has an image sensor for capturing image data of the test component 620. The image data is a digital representation of an image of the test component 620 and particularly of the colour changes of the reagents. For example, the image data includes a visual image of the test component 620. The image data may alternatively or additionally include other image-related data such as RGB (red, green, blue) data, HSL (hue, saturation, lightness) data, HSB (hue, saturation, brightness) data, HSV (hue, saturation, value) data, and histogram data.

The reader device may include an attachment mechanism for attaching to various housings of the test component 620 as described above for capturing the image data of the test component 620. For example, the reader device has a clip that clips onto the drain bag 112, transfer set tubing 106, or drain tubing 114. Clipping the reader device stabilises it and improves the quality of the image data captured by it. The mobile phone may read the test component 620 at a suitable distance/angle from it so that the image sensor is suitably focused on the test component 620. In one embodiment, the mobile phone processes the captured image data and informs the patient 102 of the substances detected in the dialysate. In another embodiment, the mobile phone does not process the captured image data but instead communicates the captured image data to a remote server that processes the captured image data. For example, the patient 102 may send the captured image data to a clinic for their processing and the clinic then communicates the detection results to the patient 102.

In some embodiments, the devices 200/300/400/500 may further include the image sensor for capturing the image data of the test component 620. For example, the image sensor is integrated with or attached to the housing of the devices 200/300/400/500. The image sensor is communicatively connectable to the electronic device such as a mobile phone so that the mobile phone is able to receive the captured image data from the image sensor. The electronic device then processes the captured image data as described above to detect the substances.

In some embodiments with reference to FIG. 8, there is a method 800 for analysing spent peritoneal dialysate. The method 800 includes a step 810 of receiving image data of a set of one or more test components 620, the image data including image test data for detecting one or more substances in the dialysate. The image data may optionally include image reference data. The method 800 includes a step 820 of comparing the image test data against the image reference data, the image test data representing reactions between the substances and one or more reagents comprised in the test components 620. The method 800 includes a step 830 of detecting the substances based on results of the comparison. The method 800 includes a step 840 of generating a message informative of the substances detected in the dialysate. The message may include visual/audio alerts or alarms to inform the patient 102 if the detected substances are in dangerous levels.

In one embodiment, the method 800 is implemented on and performed by the electronic device. The electronic device includes a processor that is configured to execute instructions, codes, computer programs, and/or scripts and includes suitable logic, circuitry, and/or interfaces to execute such instructions. A software or mobile application may be installed on the electronic device and which is executable for performing the method 800. In another embodiment, the method 800 is implemented on and performed by a remote server communicable with the electronic device. Particularly, the electronic device captures the image data and communicates the captured image data to the remote server for processing by the remote server. The remote server generates and communicates the message to the electronic device, thereby informing the patient 102 of the substances detected in the dialysate.

As stated above, the image data is a digital representation of an image of test component 620 that may include the visual image, RGB data, and/or histogram data. With reference to FIG. 7A and FIG. 7B, the image test data is a digital representation of an image of the active area 710. In one embodiment, the image reference data is comprised in the image data and is a digital representation of the inactive area 720. Having the image reference data together with the image test data prevents ambient light influence and improves the test accuracy. In another embodiment, the image reference data is not comprised in the image data but may be retrieved from memory or from a storage device communicatively linked to the electronic device/remote server performing the method 800. However, as the image reference data is absent from the image data, the image test data may be further processed to mitigate problems caused by the ambient light. It will be appreciated that such image processing will be known to the skilled person and may include the use of filters, masks, and the like.

The devices 200/300/400/500 described in various embodiments above allow patients to analyse spent peritoneal dialysate during home-based peritoneal dialysis safely and effectively. Instead of travelling to medical facilities or hospitals to receive peritoneal dialysis therapy which raise the risk of infection, these devices turn the existing peritoneal dialysis modality into a safer treatment modality by allowing patients to undergo therapy at home and monitor signs or symptoms of possible infections based on the detection results.

The devices can be integrated with a healthcare platform, such as one hosted on the remote server, that receives aggregated data of the detection results. This allows clinicians to oversee the patients' conditions and seeks to prevent infection. The healthcare platform will be able to track the detected substances across the patients and quickly identify patients who may be at risk of infections such as peritonitis. These identified patients be prescribed with antibiotics to address the infection. If peritonitis is promptly diagnosed and treated, the patients do not need to be admitted to a hospital, thus significantly reducing the hospitalisation rate and freeing up hospital space for more serious cases.

Monitoring of the detected substances can also help to gain insights as to how much of these substances are removed in one therapy, and these insights will be useful for continuous ambulatory peritoneal dialysis (CARD) and automated peritoneal dialysis (APD) therapies. The aggregation of data from these detection results will be useful for clinicians and researchers to acquire more information about the patients that may not be available currently or at least not easily availed to them. The aggregated data can lead to development of an artificial intelligence engine combined with machine learning to help predict risk factors for patients in the future.

In the foregoing detailed description, embodiments of the present disclosure in relation to devices for analysing spent peritoneal dialysate are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

The invention claimed is:

1. A device for analyzing spent peritoneal dialysate from a peritoneal dialysis apparatus, the device comprising:
   a set of housings attachable to the peritoneal dialysis apparatus;
   a set of test components disposed in the housings, each test component comprising one or more reagents for detecting one or more substances; and
   a set of fluidic conduits connected to the housings, each fluidic conduit for communicating the spent peritoneal dialysate from the peritoneal dialysis apparatus to a respective housing, each housing being sealed such that the spent peritoneal dialysate remains within the respective housing,
   wherein the test components are arranged for the reagents to react with the spent peritoneal dialysate communicated to the housings and thereby detect the substances in the spent peritoneal dialysate.

2. The device according to claim 1, wherein the fluidic conduits comprise a set of frangible seals that fluidically isolate the respective housings and are breakable to enable communication of the spent peritoneal dialysate to the respective housings.

3. The device according to claim 1, further comprising a valve mechanism for selectively controlling communication of the spent peritoneal dialysate to the respective housings.

4. The device according to claim 1, comprising:
   a plurality of the housings attachable to the peritoneal dialysis apparatus;
   a plurality of the test components disposed in the housings; and
   a plurality of fluidic conduits each connected to the respective housing.

5. The device according to claim 1, wherein the housings are attachable to the peritoneal dialysis apparatus by connecting the fluidic conduits to one of the following:
   (a) a drain bag for collecting the spent peritoneal dialysate discharged from the peritoneal dialysis apparatus;
   (b) a transfer set tubing for connecting to a catheter of the peritoneal dialysis apparatus; and
   (c) a drain tubing for discharging the spent peritoneal dialysate.

6. The device according to claim 1, wherein the housings are attachable inside a drain bag of the peritoneal dialysis apparatus for collecting the spent peritoneal dialysate discharged therefrom, the fluidic conduits arranged for communicating the spent peritoneal dialysate from the drain bag to the housings.

7. The device according to claim 6, further comprising the drain bag wherein the housings are attached inside the drain bag.

8. The device according to claim 1, wherein the fluidic conduits are configured for regulating communication of the spent peritoneal dialysate to the housings.

9. The device according to claim 1, wherein fluidic conduits comprise a set of semipermeable membranes for regulating communication of the spent peritoneal dialysate to the housings.

10. The device according to claim 1, further comprising a set of mesh components disposed in the housings for regulated wetting of the test components by the spent peritoneal dialysate.

11. The device according to claim 1, wherein the reagents comprise a combination of compounds for detecting one or more of leukocytes, glucose, urea, creatinine, and ammonia.

12. The device according to claim 1, wherein each test component comprises one or more demarcated areas, each demarcated area comprising at least one reagent for detecting a respective substance.

13. The device according to claim 12, each demarcated area further comprising:
   an active area comprising the at least one reagent for detecting the respective substance; and
   an inactive area comprising color reference data for comparing color changes in the active area,
   wherein the inactive area is optionally divided into subareas according to activity levels of the respective substance.

* * * * *